United States Patent
Abraham et al.

(10) Patent No.: US 8,889,944 B2
(45) Date of Patent: Nov. 18, 2014

(54) SENSOR PRODUCTS USING WICKING MATERIALS

(75) Inventors: Jose Kollakompil Abraham, Neenah, WI (US); Davis-Dang Hoang Nhan, Appleton, WI (US); Ning Wei, Roswell, GA (US); Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 414 days.

(21) Appl. No.: 13/312,033

(22) Filed: Dec. 6, 2011

(65) Prior Publication Data

US 2013/0144237 A1   Jun. 6, 2013

(51) Int. Cl.
*A61F 13/15*   (2006.01)

(52) U.S. Cl.
USPC .......................... 604/361; 604/359; 604/362

(58) Field of Classification Search
USPC .......................................... 604/361, 359, 362
See application file for complete search history.

(56) References Cited

U.S. PATENT DOCUMENTS

| | | | |
|---|---|---|---|
| 5,902,296 A | 5/1999 | Fluyeras | |
| 6,097,297 A | 8/2000 | Fard | |
| 6,246,330 B1 | 6/2001 | Nielsen | |
| 7,454,955 B2 | 11/2008 | Devries et al. | |
| 7,956,760 B2 | 6/2011 | Hill | |
| 2003/0020615 A1 | 1/2003 | Zand et al. | |
| 2006/0206087 A1 | 9/2006 | Lavon et al. | |
| 2008/0051745 A1 | 2/2008 | Long et al. | |
| 2008/0103414 A1 | 5/2008 | Song | |
| 2008/0147030 A1 | 6/2008 | Nhan et al. | |
| 2008/0215024 A1 | 9/2008 | Diehl et al. | |
| 2008/0269707 A1 | 10/2008 | Song | |
| 2008/0300559 A1* | 12/2008 | Gustafson et al. | 604/361 |
| 2009/0292265 A1 | 11/2009 | Helmer et al. | |
| 2010/0145294 A1 | 6/2010 | Song et al. | |
| 2010/0159611 A1 | 6/2010 | Song et al. | |
| 2010/0164733 A1 | 7/2010 | Ales et al. | |
| 2010/0304091 A1 | 12/2010 | Wang | |

FOREIGN PATENT DOCUMENTS

WO   WO 2008/024860 A2   2/2008

* cited by examiner

*Primary Examiner* — Jacqueline F. Stephens
(74) *Attorney, Agent, or Firm* — Denise L. Stoker; Randall W. Fieldhack (57) ABSTRACT

An absorbent article includes a chassis including a bodyside liner, an outer cover having an interior surface and an exterior surface, and an absorbent structure positioned adjacent the interior surface of the outer cover, the chassis including an insult zone and a crotch region positioned in between a front region and a back region, the front region and the back region defining a waist region therebetween. The absorbent article also includes a sensor element disposed in or on the chassis, the sensor element extending from a proximal end in the waist region to at least the insult zone and in fluid communication with the insult zone, the sensor element including a multi-layer wicking material.

17 Claims, 4 Drawing Sheets

SENSOR PRODUCTS USING WICKING MATERIALS

BACKGROUND

Absorbent articles such as diapers, training pants, incontinence products, feminine hygiene products, swim undergarments, and the like, conventionally include a liquid permeable body-side liner, a liquid impermeable outer cover, and an absorbent core. The absorbent core is typically located in between the outer cover and the liner for taking in and retaining liquids (e.g., urine) exuded by the wearer.

Many absorbent articles have been adapted for use in a training program, such as toilet training or enuresis control, or to provide indication of various medical, physical, or other conditions. Accordingly, various types of sensors and indicators, including moisture or wetness indicators, have been suggested for use in absorbent articles. Wetness indicators, for example, can include alarm devices that are designed to assist parents or attendants to identify a wet diaper condition upon insult. The devices produce either a visual or an audible signal.

Problems have been experienced, however, in efficiently and reliably incorporating wetness indicators into absorbent articles at the process speeds at which absorbent articles are produced. Thus, a need exists for improved wetness sensors that can be easily incorporated into absorbent articles.

Dehydration is one of the leading causes in infant mortality. Severe diarrhea can cause a 24-hour fluid loss through stools of greater than 200 milliliters per kilogram compared to a normal loss of 5 milliliters per kilogram. Severe diarrhea can also cause a 70110 millimoles/liter-water deficiency in electrolytes such as sodium and potassium. The changes of fluids and electrolytes in infants and young children can be as much as 3 times higher than that of adults due to their higher water content (approximately 70% of body weight is water in infants, 65% in children and 60% in adults).

In addition, a need also exists for sensor elements for use in a wetness indicator that are made from non-metallic materials. Incorporating metallic components into an absorbent article, for instance, can cause various problems. For instance, once the absorbent articles are packaged, the absorbent articles are typically exposed to a metal detector to ensure that no metallic contaminants have accidentally been included in the package. Making the conductive elements of a wetness indicator from a metal, however, can cause a metal detector to indicate a false positive. The incorporation of metal conductive elements into an absorbent article can also cause problems when the wearer is attempting to pass through a security gate that also includes a metal detector. Further, the presence of metal in absorbent articles inhibits or prevents reclamation of articles culled during their manufacture.

SUMMARY

The present disclosure describes a solution to electronically read dehydration as well as wetness information using an enhanced liquid wicking capillary technology. The signaling device activates when the liquid wicks through the layers of non-woven strips. The wicking material can be implemented for both active signaling (e.g., using electronic circuits) as well as passive signaling (e.g., using color changing dyes).

The present disclosure is generally directed to a wicking sensor component that can be used in numerous applications. For example, in one aspect, the wicking material can be used to form a sensor element of a wetness sensing device incorporated into an absorbent article.

The disclosure described herein solves the problems described above and provides an increase in efficacy in using wetness and other sensors in absorbent articles. In general, the present disclosure is directed to sensing absorbent articles with easy-to-use signaling devices. The signaling device, for instance, can be configured to indicate to a user that a body fluid is present in the sensing absorbent article without a pair of electrical conductors extending into the article.

In accordance with the present disclosure, the absorbent article can further include a wetness sensing device that is activated when a conductive substance is detected in the absorbent article. The wetness sensing device includes at least one fluid-conductive element, such as wicking sensor element in communication with a signaling device. The sensor element can form an open circuit within the signaling device and can be made from a multi-layer wicking material. When a conductive substance (such as urine) contacts the sensor element, the sensor element wicks fluid to the signaling device and the open circuit becomes closed, causing the signaling device to produce a signal indicating the presence of the conductive substance.

An absorbent article includes a chassis including a bodyside liner, an outer cover having an interior surface and an exterior surface, and an absorbent structure positioned adjacent the interior surface of the outer cover, the chassis including an insult zone and a crotch region positioned in between a front region and a back region, the front region and the back region defining a waist region therebetween. The absorbent article also includes a sensor element disposed in or on the chassis, the sensor element extending from a proximal end in the waist region to at least the insult zone and in fluid communication with the insult zone, the sensor element including a multi-layer wicking material.

A wetness sensing system includes an absorbent article including a chassis comprising a bodyside liner, an outer cover having an interior surface and an exterior surface, and an absorbent structure positioned adjacent the interior surface of the outer cover, the chassis including an insult zone and a crotch region positioned in between a front region and a back region, the front region and the back region defining a waist region therebetween. The system also includes a metal-free fluid conductor disposed in or on the chassis, the fluid conductor extending from a proximal end in the waist region to at least the insult zone and in fluid communication with the insult zone, the fluid conductor including a wicking material. The system also includes a signaling device configured to be removably attached to the absorbent article and configured to receive or be attachable to the proximal end of the fluid conductor, wherein the signaling device is configured to detect conductivity across the proximal end of the fluid conductor.

A wetness sensing system includes an absorbent article including a chassis including a bodyside liner, an outer cover having an interior surface and an exterior surface, and an absorbent structure positioned adjacent the interior surface of the outer cover, the chassis including an insult zone and a crotch region positioned in between a front region and a back region, the front region and the back region defining a waist region therebetween. The system also includes a metal-free fluid conductor disposed in or on the chassis, the fluid conductor extending from a proximal end in the waist region to at least the insult zone and in fluid communication with the insult zone, the fluid conductor including a multi-layer wicking material. The system also includes a signaling device configured to be removably attached to the absorbent article and configured to receive or be attachable to the proximal end of the fluid conductor, wherein the signaling device is configured to detect conductivity across the proximal end of the fluid conductor without supplying electrical current to the absorbent article Other features and aspects of the present disclosure are discussed in greater detail below.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects of the present disclosure only, and is not intended as limiting the broader aspects of the present disclosure.

The present disclosure is generally directed to sensing absorbent articles adapted to be attached to a signaling device that can be configured to indicate the presence of a body fluid in the absorbent article or other changes in the condition of the product or wearer. The absorbent article can be, for instance, a diaper, a training pant, a pre-fastened pant, a swimming pant, an incontinence product, a feminine hygiene product, a medical garment, a bandage, or any other suitable article.

The disclosure described herein can be used with any type of sensing article. In one type of sensing article used as a non-limiting example herein, wetness sensing absorbent articles can include an open circuit that becomes closed when a conductive fluid, such as a body fluid, is present in between a pair of conductive leads. Alternatively, wetness sensing absorbent articles can include a closed circuit that becomes open when a fluid, such as a body fluid, is present. Generally, the wetness sensing absorbent articles containing the circuit are disposable, meaning that they are designed to be discarded after a limited use rather than being laundered or otherwise restored for reuse.

The circuit contained within the wetness sensing absorbent articles of the present disclosure is configured to be attached to a signaling device. The signaling device can provide power to the circuit while also including some type of audible, visible, tactile, and/or electromagnetic signal that indicates to the user the presence of a body fluid. Although the wetness sensing absorbent article can itself be disposable, the signaling device can be reusable from article to article. In this regard, the present disclosure is particularly directed to different types of attachment modes that allow easy connection between the circuit in the wetness sensing absorbent article and the signaling device.

As described above, the sensor element 210 in combination with the signaling device 220 can be configured to indicate the presence of a body fluid contained within the wetness sensing absorbent article 120. The particular targeted body fluid can vary depending upon the particular type of wetness sensing absorbent article 120 and the desired application. For instance, in one aspect of the present disclosure, the wetness sensing absorbent article 120 includes a diaper, a training pant, or the like, and the signaling device 220 is configured to indicate the presence of urine. Alternatively, the signaling device 220 can be configured to indicate the hydration level of the user of the absorbent article 120. In other aspects, the signaling device 220 can be configured to indicate the presence of a yeast or of a particular constituent in urine or menses, such as a polysaccharide, a sugar, a protein, etc.

Figure 1:
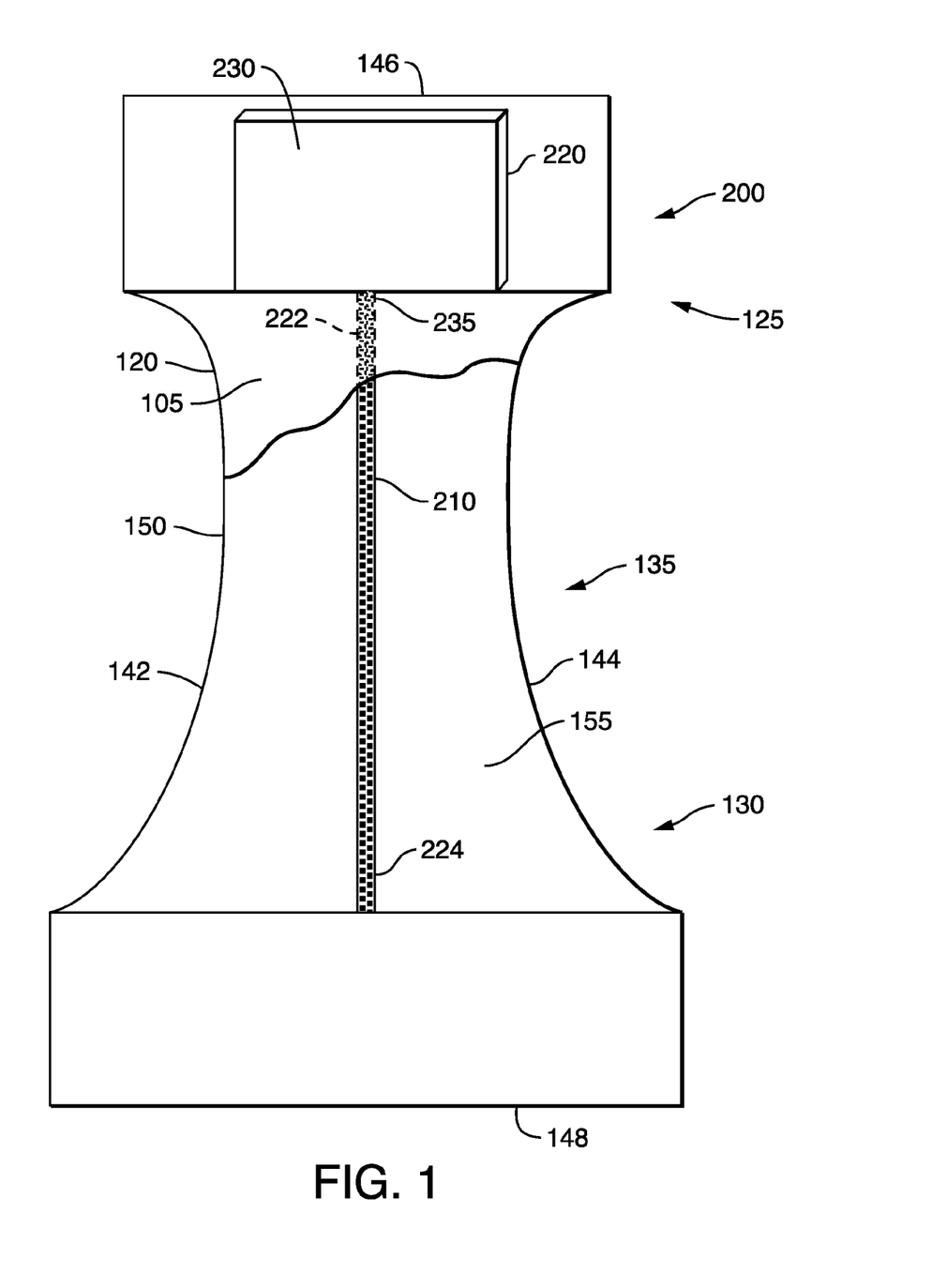
FIG. 1 is a partially cutaway laid-flat schematic view of one aspect of a garment-facing view of an absorbent article including a sensor element and a signaling device made in accordance with the present disclosure.

Referring to FIG. 1 for exemplary purposes, an absorbent article 120 that can be made in accordance with the present disclosure is shown. The absorbent article 120 might or might not be disposable.

By way of illustration only, various materials and methods for constructing absorbent articles such as the diaper 120 of the various aspects of the present disclosure are disclosed in PCT Patent Application WO 00/37009 published Jun. 29, 2000 by A. Fletcher et al.; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al., which are incorporated herein by reference to the extent they are consistent (i.e., not in conflict) herewith.

A generic garment-type absorbent article 120 is representatively illustrated in FIG. 1. The garment-type absorbent article 120 defines a pair of longitudinal end regions, otherwise referred to herein as a front region 125 and a back region 130, and a center region, otherwise referred to herein as a crotch region 135, extending longitudinally between and interconnecting the front and back regions 125, 130. The garment-type absorbent article 120 also defines an inner surface adapted in use (e.g., positioned relative to the other components of the article) to be disposed toward the wearer, and an outer surface opposite the inner surface. The front and back regions 125, 130 are those portions of the garment-type absorbent article 120 that, when worn, wholly or partially cover or encircle the waist or mid-lower torso of the wearer. The crotch region 135 generally is that portion of the garment-type absorbent article 120 that, when worn, is positioned between the legs of the wearer and covers the lower torso and crotch of the wearer. The garment-type absorbent article 120 has a pair of laterally opposite side edges 142, 144 and a pair of longitudinally opposite waist edges, respectively designated front waist edge 146 and back waist edge 148.

The illustrated garment-type absorbent article 120 includes a chassis 150 that, in this aspect, encompasses the front region 125, the back region 130, and the crotch region 135.

The chassis 150 includes an outer cover 105 and a bodyside liner (not shown) that can be joined to the outer cover 105 in a superimposed relation therewith and an absorbent structure 155 disposed between the outer cover 105 and the bodyside liner for absorbing liquid body exudates from the wearer. The chassis 150 can further include a pair of containment flaps (not shown) secured to the bodyside liner for inhibiting the lateral flow of body exudates.

The elasticized containment flaps define a partially unattached edge that assumes an upright configuration in at least the crotch region 135 of the garment-type absorbent article 120 to form a seal against the wearer's body. The containment flaps can extend longitudinally along the entire length of the chassis 150 or can extend only partially along the length of the chassis 150. Suitable constructions and arrangements for the containment flaps are generally well known to those skilled in the art.

To further enhance containment and/or absorption of body exudates, the garment-type absorbent article 120 can also suitably include leg elastic members (not shown), as are known to those skilled in the art. The leg elastic members can be operatively joined to the outer cover 105 and/or the bodyside liner and positioned in the crotch region 135 of the garment-type absorbent article 120. The leg elastic members can be formed of any suitable elastic material.

In some aspects, the garment-type absorbent article 120 can further include a surge management layer (not shown) that can be optionally located adjacent the absorbent structure and attached to various components in the garment-type absorbent article 120, such as the absorbent structure 155 or the bodyside liner, by methods known in the art, such as by using an adhesive. A surge management layer helps to decelerate and diffuse surges or gushes of liquid that can be rapidly introduced into the absorbent structure 155 of the garment-type absorbent article 120. Desirably, the surge management layer can rapidly accept and temporarily hold the liquid prior to releasing the liquid into the storage or retention portions of the absorbent structure 155.

The garment-type absorbent article 120 can further include a pair of opposing elastic side panels (not shown) that are attached to the back region 130 of the chassis 150. The side panels can be stretched around the waist and/or hips of a wearer to secure the garment-type absorbent article 120 in place. The side panels can be attached or bonded to the chassis 150 using any suitable bonding technique. In an alternative aspect, the elastic side panels can also be integrally formed with the chassis 150. For instance, the side panels can be an extension of the bodyside liner, of the outer cover 105, or of both the bodyside liner and the outer cover 105. The elastic side panels each have a longitudinal outer edge, a leg end edge disposed toward the longitudinal center of the training pant, and waist end edges disposed toward a longitudinal end of the garment-type absorbent article 120.

The front and back regions 125, 130 of the garment-type absorbent article 120 can be connected by a fastening system (not shown) to define a three-dimensional configuration having a waist opening and a pair of leg openings. The waist opening of the garment-type absorbent article 120 is defined by the waist edges 146, 148 and encircles the waist of the wearer.

The side panels, if present, can be releasably attachable to the front region 125 of the article by the fastening system. It should be understood, however, that in other aspects, the side panels can be permanently joined to the chassis 150 at each end. The side panels can be permanently bonded together, for instance, when forming a training pant or absorbent swimwear.

The fastening system can include laterally opposite first fastening components (not shown) adapted for refastenable engagement to corresponding second fastening components. The fastening components can be any refastenable fasteners suitable for absorbent articles.

The garment-type absorbent article 120 can include various waist elastic members (not shown) for providing elasticity around the waist opening. For example, the garment-type absorbent article 120 can include a front waist elastic member and/or a back waist elastic member.

The materials used to form the garment-type absorbent article 120 that surround the waist elastic members can vary depending upon the particular application and the particular product being produced.

The outer cover 105, for instance, can be breathable and/or can be liquid impermeable. The outer cover 105 can be constructed of a single layer, multiple layers, laminates, spunbond fabrics, films, meltblown fabrics, elastic netting, microporous webs, bonded-carded webs or foams provided by elastomeric or polymeric materials. The outer cover 105, for instance, can be a single layer of a liquid impermeable material, or alternatively can be a multi-layered laminate structure in which at least one of the layers is liquid impermeable. In other aspects, however, it should be understood that the outer cover 105 can be liquid permeable. In this aspect, for instance, the garment-type absorbent article 120 can contain an interior liquid barrier layer.

The inner layer of the outer cover 105 can be both liquid and vapor impermeable, or it can be liquid impermeable and vapor permeable. The inner layer can be manufactured from a thin plastic film, although other flexible liquid impermeable materials can also be used. The inner layer, or the liquid impermeable outer cover when a single layer, prevents waste material from wetting articles, such as bed sheets and clothing, as well as the wearer and caregiver.

The bodyside liner is suitably compliant, soft-feeling, and non-irritating to the wearer's skin. The bodyside liner is also sufficiently liquid permeable to permit liquid body exudates to readily penetrate through its thickness to the absorbent structure 155.

The absorbent structure 155 can be disposed between the outer cover 105 and the bodyside liner. The absorbent structure 155 can be any structure or combination of components that are generally compressible, conformable, non-irritating to a wearer's skin, and capable of absorbing and retaining liquids and certain body wastes. As a general rule, superabsorbent material is present in the absorbent web in an amount of from about 0 to about 90 weight percent based on total weight of the web. Superabsorbent materials are well known in the art.

After being formed or cut into a desired shape, the absorbent web material can be wrapped or encompassed by a suitable tissue or meltblown web or the like wrap sheet that aids in maintaining the integrity and shape of the absorbent structure 155. The absorbent web material can also be a coform material.

In various aspects of the present disclosure, the garment-type absorbent article 120 can include additional features such as those disclosed in co-pending and co-assigned U.S. patent application Ser. No. 11/303,283 to Long, et al. and entitled "Garments With Easy-To-Use Signaling Device"; and U.S. patent application Ser. No. 11/215,937 to Ales, et al. and entitled "Method of Detecting the Presence of an Insult in an Absorbent Article and Device for Detecting the Same"; which are incorporated herein by reference to the extent they are consistent (i.e., not in conflict) herewith. For example, the garment-type absorbent article 120 can also include other wetness sensing features such as fading ink, appearing ink, a wetness liner, or a cooling component.

Figure 2:
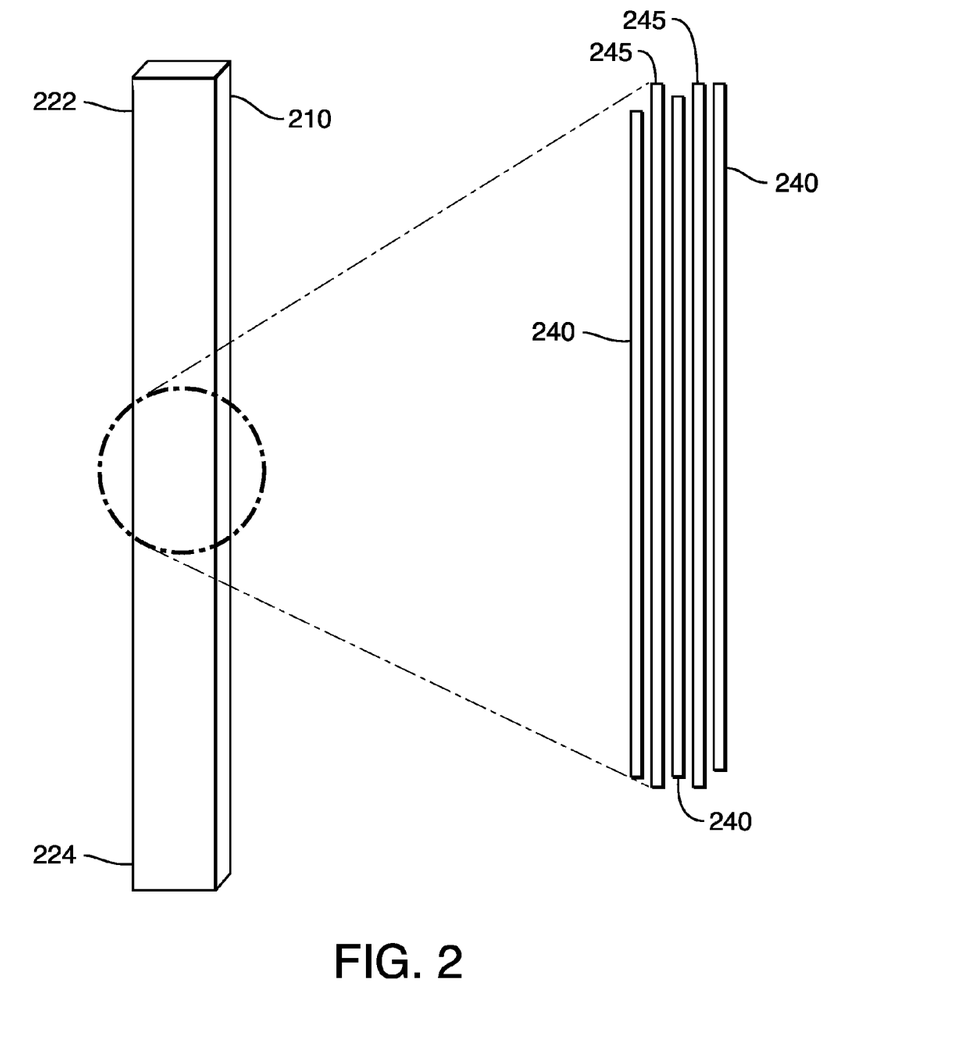
FIG. 2 is an expanded schematic view of the sensor element of FIG. 1.
Figure 3:
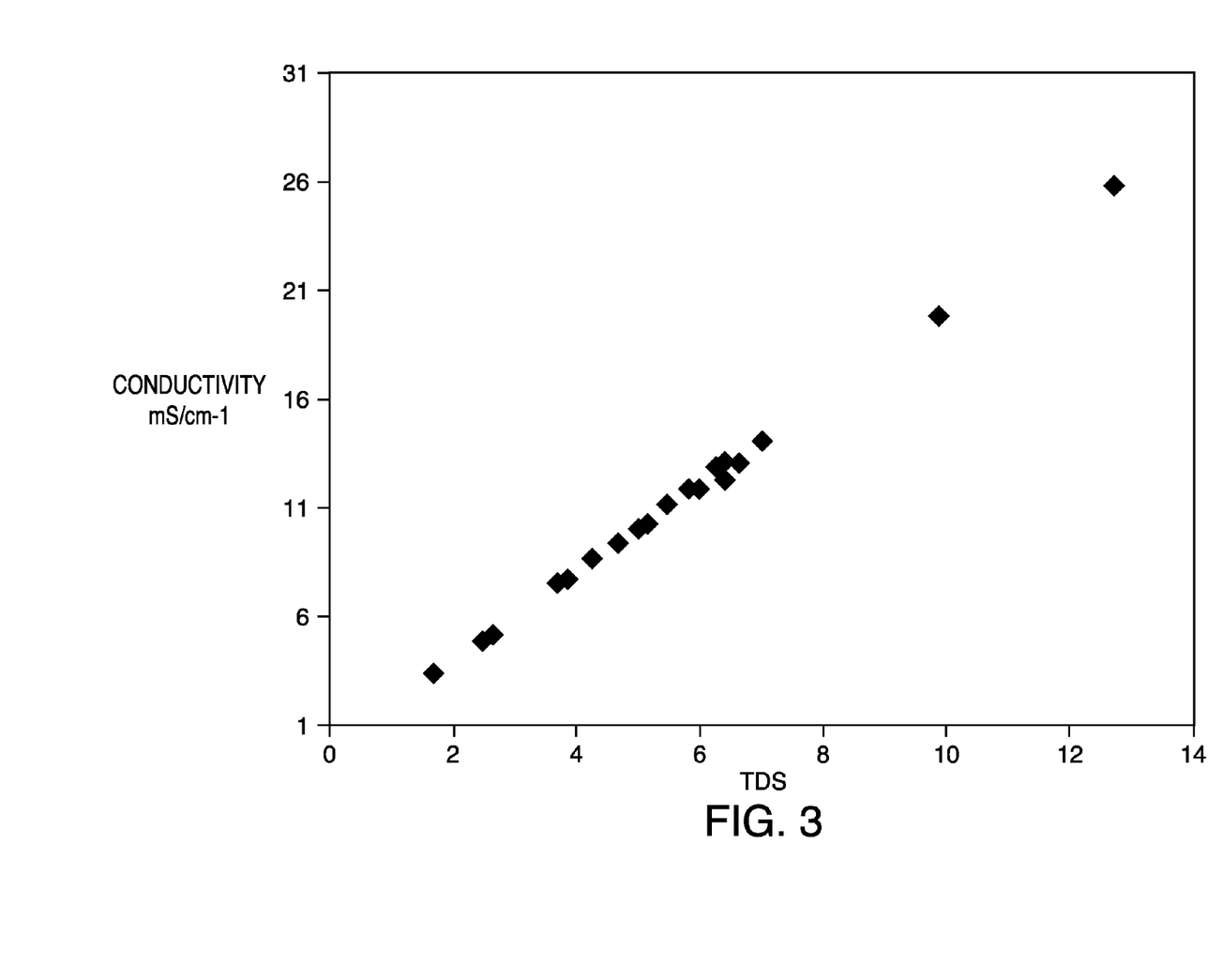
FIG. 3 is a graphic representation of conductivity as a function of measured total dissolved solids (TDS) from adult urine samples.

As described above, the present disclosure is particularly directed to incorporating a body fluid indicating system 200, such as a wetness sensing device, into the absorbent article 120. In this regard, as shown in FIGS. 1 and 2, the absorbent article 120 includes a sensor element 210. The sensor element 210 has a proximal end 222 and a distal end 224. In this aspect, the sensor element 210 extends from the front region 125 of the absorbent article 120 to the back region 130. In accordance with the present disclosure, the sensor element 210 can be made from a material as described below.

In the aspect shown in FIG. 1, the sensor element 210 extends the entire length of the absorbent article 120. It should be understood, however, that in other aspects the sensor element 210 can extend only to the crotch region 135 or can extend to any particular place in the absorbent article 120 where a body fluid is intended to be sensed. The sensor element 210 can be limited to or can extend beyond an insult zone, the area in which an insult is expected or most probable in the absorbent article 120.

The sensor element 210 can be incorporated into the chassis 150 at any suitable location as long as the sensor element 210 is positioned so as to contact a body fluid that is absorbed by the absorbent article 120. In this regard, the sensor element 210 generally lies inside the outer cover 105. In fact, in one aspect, the sensor element 210 can be attached or laminated to the inside surface of the outer cover 105 that faces the absorbent structure 155. Alternatively, however, the sensor element 210 can be positioned on the absorbent structure 155 or positioned on the liner. The sensor element 210 can be configured to be disposed on or in the absorbent article 120 by a consumer or by the manufacturer of the absorbent article 120.

The electrical conductivity of a liquid is directly proportional to the amount of salts dissolved in it. Conductivity is a measure of a sample's ability to pass electrical current using movable charges. The amount of minerals or salts dissolved in a liquid is called Total Dissolved Solids (TDS), which is measured in parts per million. Concentrations of dissolved salts and minerals in pure water is typically very low, making the electrical conductivity of the water very low as well. Electrical conductivity is expressed as mhos per centimeter (M/cm), or siemens per centimeter (S/cm). Because a mho (or siemen) is a very large unit, the micromho (microsiemen) or millimho (millisiemen) is typically used (mS/cm).

Clinical studies have shown that significant changes in post-race sodium levels occur due to the liquid body weight loss (e.g., 2.5 kg) in full course triathlons. The state of negative fluid balance causes a change in electrolyte levels due to the change in body weight. As a result, sodium and potassium are good markers for dehydration monitoring. A non-invasive method to monitor hydration levels in infant and adult care absorbent articles at the point of care/use is highly desirable. Measured results using a spontaneous wicking layer in conjunction with a signaling device 220 have demonstrated their efficacy in monitoring changes in electrolytes and therefore heath states when used with absorbent articles.

Further clinical studies have shown that urine conductivity and specific gravity are related to hydration status in young as well as adult populations. Renal functions were evaluated based on conductivity of urine, wherein morning urine samples collected from subjects were evaluated for osmolality, conductivity, specific gravity, pH, and salt levels of sodium, potassium, chloride, phosphates, and calcium. The study found significant relations between osmolality, conductivity, and specific gravity with salt concentrations of the collected samples. Conductivity is positively related to osmolality, sodium, and uric acid concentrations. While osmolality and specific gravity are affected primarily by non-electrolytic molecules, conductivity is only related to sodium and uric acid concentrations. The study suggests that conductivity can be used as a parameter for routine urinalysis.

Osmolality is a measure of solute concentration in a liquid. Osmolality is a measure of osmoles of solutes per kilogram of solvent. Osmolality and conductivity studies of urine have proved that a better relationship exists between Na+ concentration and conductivity than between Na+ concentration and osmolality. Usually osmolality does not respond in the presence of large quantities of glucose in the urine. However, close correlation between conductivity and Na+ concentration remains and hence conductometry is preferred to osmolality in clinical analysis for diabetic patients.

A spontaneous wicking technology can be used to indicate health state of the wearer as well as wetness status from urine conductivity measurements at the waist band. This indication is an electronic indication based on a spontaneous wicking and transporting of fluids through a double layer capillary action, which eliminates the requirement to use any conducting or resistive electrodes in absorbent articles. It has been observed that the speed of liquid transport in regular wicking material can be increased by using a multi-layer wicking design (FIG. 2). The intermolecular adhesion and cohesion forces are altered and the wicking speed is enhanced in the current multilayer design as shown in FIG. 2. The advantage is the use of a single metal-free strip for electronic sensing as shown in FIG. 1.

Capillary action is macroscopic flow of liquid under the interfacial forces in narrow tubes. The surface tension due to intermolecular forces of adhesion and cohesion causes the molecules to flow. Capillary wicking mechanism allows unforced flow of liquids due to capillary force. Wicking materials use capillary action to pull water particles against the gravity. The capillary action creates liquid flow from much more concentrated areas to less concentrated areas in the wicking strip. The capillary action continues until the wicking strip reaches an equilibrium saturation profile.

One of the problems in sensing with wicking strips is the slowness due to the inability to achieve a high rate of fluid wicking or to achieve a faster time. As a result, in most cases wetness detection using wicking strips fails to inform the user within a reasonable time. It has been observed that instead of using a single strip wicking material for wetness sensing, the multi-strip system reduces the wicking time more than half that of that of a single strip.

The measured results show that the double layer action pulls the moisture more than 2 times faster than that of a single layer capillary action. The rapid capillary action layer in this design has three wicking layers 240 separated with intermediate layers 245 that enhance capillarity in materials. Spontaneous wettability is achieved in this multi-layered structure using the capillary forces at the fibers as well as between the layers 240, 245. The intermediate layers 245 can be made from any suitable material with suitable properties and permittivities.

The wicking material can be any suitable material, such as a tissue, nonwoven, cellulosic materials, glass fiber materials, treated nonwovens, synthetic fibers, natural fibers, open-celled foam, or the like. Suitable material and construction of the wicking layer can be chosen such that a liquid will move quickly along the wicking strip. This speed at which a liquid moves through the wicking material may be measured using the vertical wicking test as described in U.S. Pat. No. 8,053, 625 B2, which is incorporated herein by reference to the extent it does not conflict herewith. The wicking material can have a vertical wicking speed of at least 1.3 inches/min. Examples include GF/DVA and LF1 available from GE Healthcare, and 75 gsm tissue available from Kimberly-Clark Corporation, using an uncreped through air dry tissue process.

Figure 4:
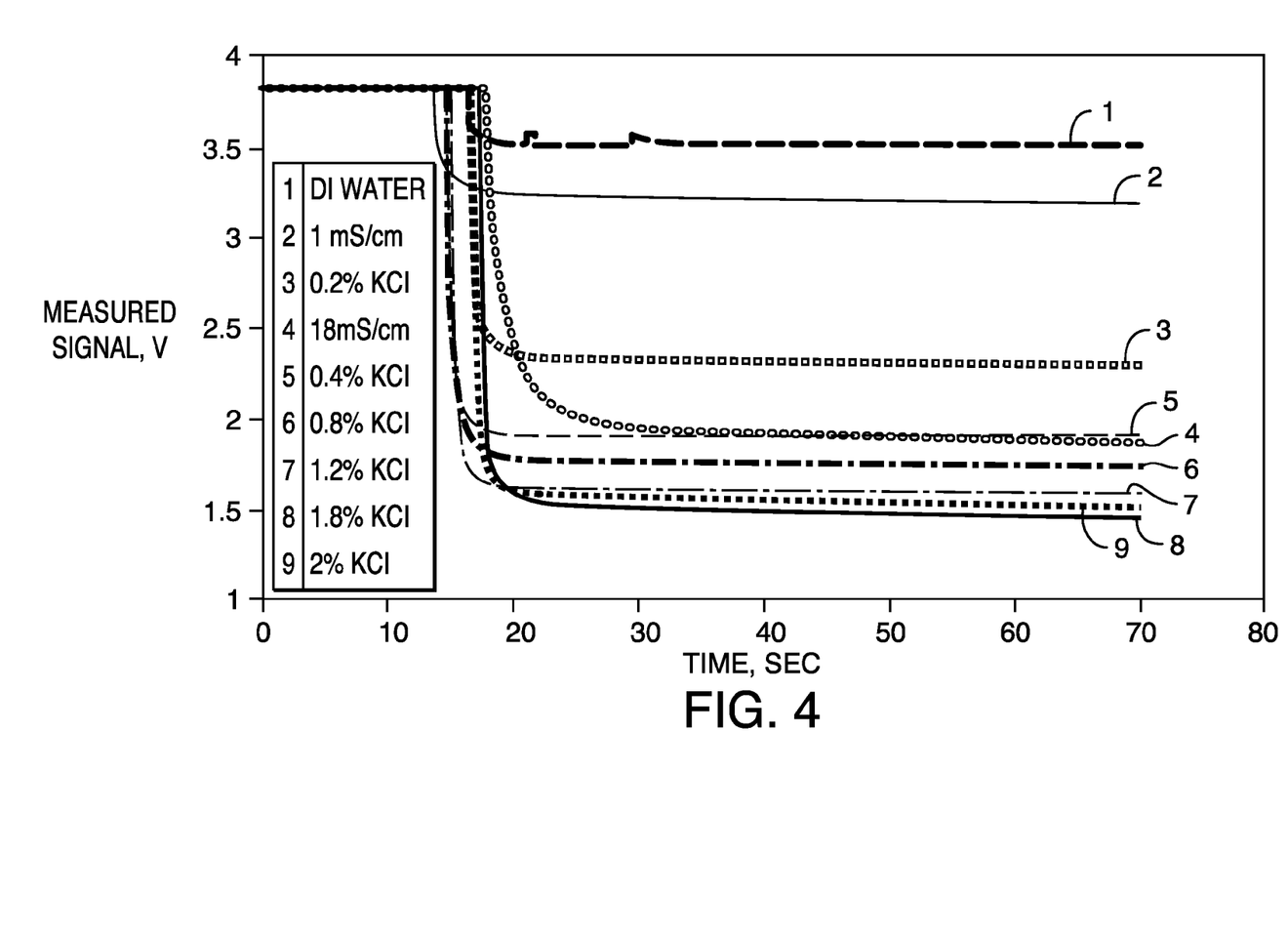
FIG. 4 is a graphic representation of the measured change in output voltage for samples of different TDS along with control (DI=deionized water).

An electrical signal detection circuit 230 in the signaling device 220 can read any changes in the conductivity of the sensor element 210 at the waist zone and detect the wetness and hydration, among other health-related parameters, by measuring the change in conductivity. An initial change in conductivity in the sensor element 210 indicates that wetness due to an insult has occurred. The extent of the change in conductivity over time indicates the concentration of total dissolved solids in the urine, and therefore the hydration level of the wearer as discussed in more detail below. In other words, the body fluid indicating system 200 also monitors dehydration by measuring the change in conductivity of the urine, which is directly related to the change in concentration of various electrolytes. FIG. 4 presents the measured change in voltage due to the change in concentration of KCl in a solution using the multi-layer wicking material.

A study conducted to evaluate the significance of urine conductivity by using the Sismex UF-100 analyzer in correlation with other parameters such as osmolality and renal diuresis, relative density, electrolytes and creatinine concentration demonstrated that urine conductivity is related to ionic concentration but not to glucose and/or protein presence and hence it is recommended for the urine analysis of diabetic patients.

Referring to FIG. 1 for exemplary purposes, a signaling device 220 is shown attached to the absorbent article 120. The signaling device 220 includes an aperture 235 into which the proximal end 222 of the sensor element 210 is inserted. When a body fluid is present in the absorbent article 120 and therefore the sensor element 210, the open circuit formed by the connection of the electrical signal detection circuit 230 across the sensor element 210 is closed by the presence of a conductive fluid. The closed circuit then, in turn, activates the signaling device 220.

The signaling device 220 can emit any suitable signal to indicate to the user that the circuit has been closed. The electrical signal detection circuit 230 also measures the conductivity change across the proximal end 222 of the sensor element 210 over time to determine the concentration of TDS in the urine and therefore the hydration level of the wearer.

These and other modifications and variations to the present disclosure can be practiced by those of ordinary skill in the art, without departing from the spirit and scope of the present disclosure, which is more particularly set forth in the appended claims. In addition, it should be understood that aspects of the various aspects of the present disclosure can be interchanged either in whole or in part. Furthermore, those of ordinary skill in the art will appreciate that the foregoing description is by way of example only, and is not intended to limit the disclosure so further described in such appended claims.

What is claimed:

1. An absorbent article comprising:
a chassis comprising a bodyside liner, an outer cover having an interior surface and an exterior surface, and an absorbent structure positioned adjacent the interior surface of the outer cover, the chassis including an insult zone and a crotch region positioned in between a front region and a back region, the front region and the back region defining a waist region therebetween;
a sensor element disposed in or on the chassis, the sensor element extending from a proximal end in the waist region to at least the insult zone and in fluid communication with the insult zone, the sensor element including a multi-layer wicking material;
wherein the multi-layer wicking material includes two wicking layers separated by a barrier layer.

2. The absorbent article of claim 1, wherein the proximal end of the sensor element is configured to be insertable or attachable to a signaling device.

3. The absorbent article of claim 1, further comprising a signaling device configured to be removably attached to the absorbent article and configured to receive or be attachable to the proximal end of the sensor element.

4. The absorbent article of claim 3, wherein the signaling device is configured to detect conductivity across the proximal end of the sensor element.

5. The absorbent article of claim 4, wherein the signaling device is configured to generate a signal when the conductivity increases.

6. The absorbent article of claim 5, wherein the signal is auditory, visual, tactile, radiofrequency, or a combination thereof.

7. The absorbent article of claim 1, wherein the sensor element is disposed adjacent the outer cover.

8. The absorbent article of claim 1, wherein the sensor element is disposed adjacent the bodyside liner.

9. An absorbent article comprising:
a chassis comprising a bodyside liner, an outer cover having an interior surface and an exterior surface, and an absorbent structure positioned adjacent the interior surface of the outer cover, the chassis including an insult zone and a crotch region positioned in between a front region and a back region, the front region and the back region defining a waist region therebetween;
a sensor element disposed in or on the chassis, the sensor element extending from a proximal end in the waist region to at least the insult zone and in fluid communication with the insult zone, the sensor element including a multi-layer wicking material;
wherein the multi-layer wicking material includes three wicking layers separated by barrier layers.

10. A wetness sensing system comprising
an absorbent article comprising:
a chassis comprising a bodyside liner, an outer cover having an interior surface and an exterior surface, and an absorbent structure positioned adjacent the interior surface of the outer cover, the chassis including an insult zone and a crotch region positioned in between a front region and a back region, the front region and the back region defining a waist region therebetween, and
a metal-free fluid conductor disposed in or on the chassis, the fluid conductor extending from a proximal end in the waist region to at least the insult zone and in fluid communication with the insult zone, the fluid conductor including a multi-layered wicking material wherein the multi-layer wicking material includes two or three wicking layers separated by barrier layers; and
a signaling device configured to be removably attached to the absorbent article and configured to receive or be attachable to the proximal end of the fluid conductor, wherein the signaling device is configured to detect conductivity across the proximal end of the fluid conductor.

11. The system of claim 10, wherein the signaling device is configured to generate a signal when the conductivity increases.

12. The system of claim 11, wherein the signal is auditory, visual, tactile, radiofrequency, or a combination thereof.

13. The system of claim 10, wherein the fluid conductor is configured to be disposed on the chassis by a consumer.

14. The system of claim 10, wherein the fluid conductor is configured to be disposed on the chassis by a manufacturer of the absorbent article.

15. The system of claim 10, wherein the fluid conductor is disposed adjacent the outer cover.

16. The system of claim 10, wherein the fluid conductor is disposed adjacent the bodyside liner.

17. The system of claim 10, wherein the wicking material has a vertical wicking speed of at least 1.3 inches/min.

* * * * *